US008599388B1

(12) United States Patent
van Dijk et al.

(10) Patent No.: US 8,599,388 B1
(45) Date of Patent: Dec. 3, 2013

(54) COHERENT OPTICAL MAPPING OF PARTICLES

(71) Applicant: The Board of Trustees of the University of Illinois, Urbana, IL (US)

(72) Inventors: Thpomas van Dijk, Urbana, IL (US); David Mayerich, Savoy, IL (US); Rohit Bhargava, Urbana, IL (US); Paul Scott Carney, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 13/667,287

(22) Filed: Nov. 2, 2012

(51) Int. Cl.
*G01B 11/14* (2006.01)

(52) U.S. Cl.
USPC ........... 356/620; 356/302; 356/301; 356/326; 506/9

(58) Field of Classification Search
USPC ................. 356/302, 620, 301, 326; 506/9
See application file for complete search history.

(56) References Cited

U.S. PATENT DOCUMENTS

2007/0194225 A1* 8/2007 Zorn .......................... 250/306
2012/0046191 A1* 2/2012 Vu et al. ...................... 506/9

OTHER PUBLICATIONS

Gunewardene et al., "Superresolution Imaging of Multiple Fluorescent Proteins with Highly Overlapping Emission Spectra in Living Cells," *Biophys. J.*, vol. 101, No. 6, pp. 1522-1528 (Sep. 2011).
Testa et al., "Multicolor Fluorescence Nanoscopy in Fixed and Living Cells by Exciting Conventional Fluorophores with a Single Wavelength," *Biophys. J.*, vol. 99, No. 8, pp. 2686-2694 (Oct. 2010).

* cited by examiner

*Primary Examiner* — Gregory J Toatley
*Assistant Examiner* — Iyabo S Alli
(74) *Attorney, Agent, or Firm* — Suntein Kann Murphy & Timbers LLP

(57) ABSTRACT

Methods and computer program products for super-resolution mapping of nanoprobes having spectrally distinguishable coherent scattering properties. A sample containing a plurality of nanoprobes is illuminated with broadband light, and coherent scattering by the nanoprobes is detected. Scattered light is spectrally associated with respective nanoprobes, allowing a position associated with each nanoprobe to be mapped.

9 Claims, 6 Drawing Sheets

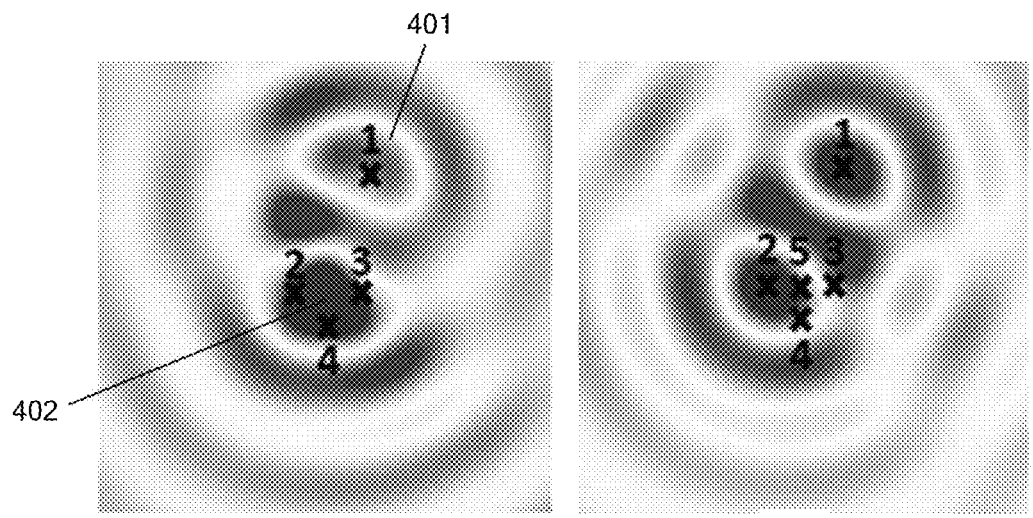
*FIG. 4A*     *FIG. 4B*
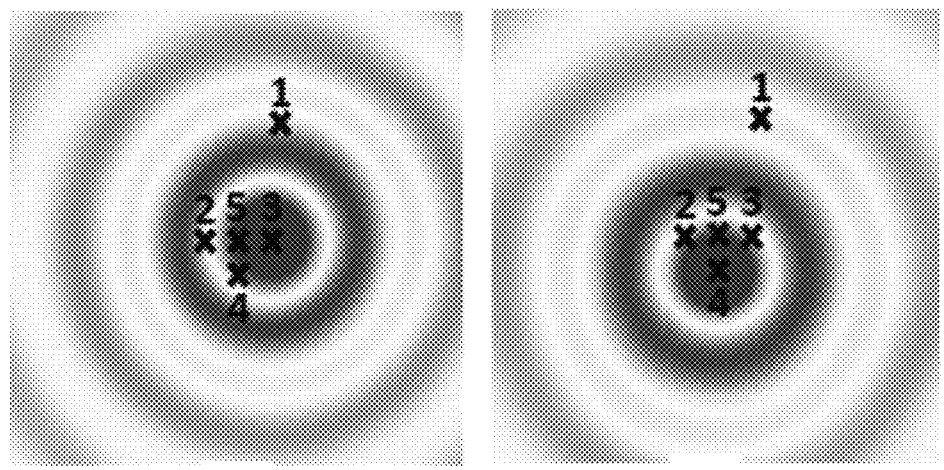
*FIG. 4C*     *FIG. 4D*

COHERENT OPTICAL MAPPING OF PARTICLES

Portions of this invention were developed with Government support under grant CHE0957849, awarded by the National Science Foundation. The Government has certain rights in the invention.

TECHNICAL FIELD OF THE INVENTION

The present invention pertains to imaging dynamical systems at nanometer resolution by means of nanoprobes with distinguishable spectral responses, and, more particularly, to mapping of nanoprobes on the basis of coherent scattering.

BACKGROUND OF THE INVENTION

Subcellular structures are unresolvable by classical optical techniques as such structures are smaller than the resolution limit, as described by Abbe, *Beiträge zur Theorie des Mikroskops and der mikroskopischen Wahrnehmung, Arch. Mikroskop. Anat.* 9, 413-18 (1873). Super-resolved fluorescence microscopy techniques have been developed to overcome this long-standing far-field resolution barrier in recent years, as described by Hell, et al., *Far-field optical nanoscopy, Science* 316, 1153-58 (2007), and can be divided into two major approaches. One approach relies on a nonlinear optical response to reduce the width of the point spread function either directly or in post-acquisition image synthesis. The best developed example of such a technique is stimulated-emission-depletion fluorescence microscopy (STED) in which a second laser depletes excited fluorophores that are farthest away from the focal spot, described by Hell, et al., *Breaking the diffraction resolution limit by stimulated emission: stimulated-emission-depletion fluorescence microscopy, Opt. Lett.* 19, 780-82 (1994).

A second approach circumvents the usual resolution limits by trans-forming imaging into a mapping problem. While imaging is a problem of estimating the components of a vector in an infinite-dimensional Hilbert space, and is limited by bandwidth, mapping is a series of problems each requiring an estimate of two or three components of a vector in a two- or three-dimensional Hilbert space and limited by signal-to-noise ratio (SNR). This reduction in dimensionality of the problem is achieved by limiting the number of active fluorescent probes in the focal region to one. Switchable fluorescent probes provide such control, enabling separation of individual probes in the time domain from spatially overlapping fluorescent images. For each activated probe the position is calculated by finding the center of the imaged spot. A complete image is subsequently built by acquiring a series of subimages. High-precision mapping of probes was independently implemented as PALM (photo activated localization microscopy, described by Betzig, et al., *Imaging Intracellular Fluorescent Proteins at Nanometer Resolution, Science,* 313, 1642-45 (2006)), STORM (Rust, et al., *ISub-diffraction-limit imaging by stochastic optical reconstruction microscopy (STORM), Nat. Methods,* 3, 793-95 (2006)), and FPALM (Hess, et al., *Ultra-High Resolution Imaging by Fluorescence Photoactivation Localization Microscopy, Biophys. J.,* 91, 4258-72 (2006)). The location of the individual probes can be estimated with a higher precision than the diffraction limit The sequential localization of the fluorescent probes, subsequently, builds up the final map over time. The localization precision is proportional to $\propto 1/\sqrt{N}$, where N is the number of detected photons. Thus, increased resolution requires longer measurements.

As a consequence of the fact that spatial mapping precision depends on the isolation of emission events in time, the major limiting factor of PALM/STORM methods is the intrinsic trade-off between spatial and temporal resolution, making them slower and less suitable than conventional microscopy for dynamic samples. While spatial resolution may be improved by measuring for a longer period, this leads to a reduced temporal resolution. Applications are therefore mainly limited to static or slowly-changing samples.

Strand-like tissue such as microtubules have become a benchmark structure for gauging spatial resolution. Including fluorescent probes with spectrally distinct emission spectra has allowed for parallel acquisition and improves imaging times, as discussed by Gunewardene, et al., *Superresolution Imaging of Multiple Fluorescent Proteins with Highly Overlapping Emission Spectra in Living Cells Biophys. J.,* 101, 1522-28 (2011), incorporated herein by reference. To date the number of differently colored dyes being imaged simultaneously has been limited to four, due to technological challenges discussed by Testa, et al., *Multicolor Fluorescence Nanoscopy in Fixed and Living Cells by Exciting Conventional Fluorophores with a Single Wavelength, Biophys. J.,* 99, 2686-94 (2010). As a result, resolution in PALM/STORM approaches has reached a practical limit dictated by the intrinsic properties of the process as well as by available technology.

SUMMARY OF CERTAIN EMBODIMENTS OF THE INVENTION

In accordance with preferred embodiments of the present invention, methods and computer program products are provided for simultaneously mapping positions of a plurality of spectrally distinguishable nanoprobes with resolution greater than diffraction-limited resolution. The methods have steps of:

a. illuminating the plurality of nanoprobes with an illuminating electromagnetic wave;
b. detecting light scattered by the plurality of nanoprobes;
c. spectrally associating scattered light with respective nanoprobes; and
d. mapping, based on a single measurement, a position associated with each nanoprobe.

In accordance with further embodiments of the invention, the spectrally distinguishable nanoprobes may be linked to at least one specified analyte. The spectrally distinguishable nanoprobes may be microspheres. The step of spectrally associating may include projection of the total signal onto a spectral response of each nanoprobe at each of a plurality of pixels. THe spectral association may also include spectrally associating inelastically scattered light.

In accordance with other embodiments of the invention, mapping a position may include mapping a position in three dimensions.

In an alternate embodiment of the present invention, a computer program product is provided for use on a computer system for mapping positions of a plurality of nanoprobes embedded within a sample. The computer program product has a computer usable medium having computer-readable non-transitory program code thereon, which includes:

a. program code for spectrally associating scattered light with respective nanoprobes; and
b. mapping, based on a single measurement, a position associated with each nanoprobe.

In other embodiments, spectrally associating may include projection of the total signal onto a spectral response of each nanoprobe at each of a plurality of pixels, and mapping a position may include mapping a position in three dimensions.

DESCRIPTION OF THE FIGURES

The foregoing features of the invention will be more readily understood by reference to the following detailed description, taken with reference to the accompanying drawings, in which:

FIGS. 4A-4E depict absorbance images of four 50-nm spheres at locations 1, 2, 3, and 4. In FIG. 4A, all four spheres are composed of the same material with a resonance peak at 425 nm. FIGS. 4B-4D show absorbance images taken at 425 nm, 500 nm, and 550 nm, respectively, corresponding to resonance peaks of distinct spheres, as described in the text. Spheres 1 and 2 have a resonance peak at 425 nm, sphere 3 has a resonance peak at 500 nm, and sphere 4 has a resonance peak at 550 nm. Absorbance images are shown at 425 nm (FIG. 4B), 500 nm (FIG. 4B), and 550 nm (FIG. 4D), corresponding to the resonance peaks of each material. FIG. 4E shows spectra from each indicated point is shown, offset for clarity.

FIG. 5A shows the integrated intensity, the image that would be recorded with a conventional microscope, while FIG. 5B shows mapped locations of the spheres, after adding Gaussian noise to provide a SNR≈10, in a field of view of 0.25 μm×0.2 μm.

DESCRIPTION OF SPECIFIC EMBODIMENTS OF THE INVENTION

Definitions

As used in this description and the accompanying claims, the following terms shall have the meaning indicated, unless the context otherwise requires:

The term "image" shall mean any multidimensional representation, whether in tangible or otherwise perceptible form or otherwise, whereby a value of some characteristic is associated with each of a plurality of locations corresponding to dimensional coordinates of an object in physical space, though not necessarily mapped one-to-one thereonto. Thus, for example, the graphic display of the spatial distribution of some feature, such as intensity, or phase, constitutes an image. So, also, does an array of numbers in a computer memory or holographic medium. Similarly, "imaging" refers to the rendering of a stated physical characteristic in terms of one or more images.

The term "map" shall refer to any determination and representation, in a tangible and non-transitory medium, of a position in terms of spatial coordinates, or, when used in an algebraic sense, shall refer to a correspondence between vectors in one space and vectors in another space.

The term "broadband," as applied to a source of radiation, shall mean a source for which $\Delta k/k_0$ is at least 3%, with $k_0$ denoting the central wavenumber of the spectrum illuminating a sample, which $\Delta h$ denotes the range of illuminating wave numbers.

The term "nanoparticle" shall refer to any deeply subwavelength structure physically distinct from it's environment. In experiments with visible light, this includes particles with linear dimensions up to a few hundred nanometers, but typically just tens of nanometers. Insofar as a nanoparticle may be used as a probe, in accordance with the present invention, it may be referred to, herein, interchangeably, as a "nanoprobe."

In accordance with certain embodiments of the present invention, methods are taught for rapid super-resolved mapping of nanoprobes. The methods rely on computed localization of isolated probes, analogous to the methods, described above, of photoactivation localization microscopy (PALM), stochastic optical reconstruction microscopy (STORM), and fluorescence photoactivation localization microscopy (FPALM), referred to collectively here as PALM/STORM. Rather than isolating individual fluorescent emission events in time, as in the prior art, methods in accordance with the present invention identify the signal from individual nanoprobes in the spectral domain, thereby advantageously overcoming the limited temporal resolution of current fluorescence microscopy techniques.

The PALM/STORM methods may be seen as embedding an N-dimensional mapping problem in N+1 dimensions and relying on each event in N dimensions to be mapped uniquely to a coordinate in the extra dimension.

Figure 1:
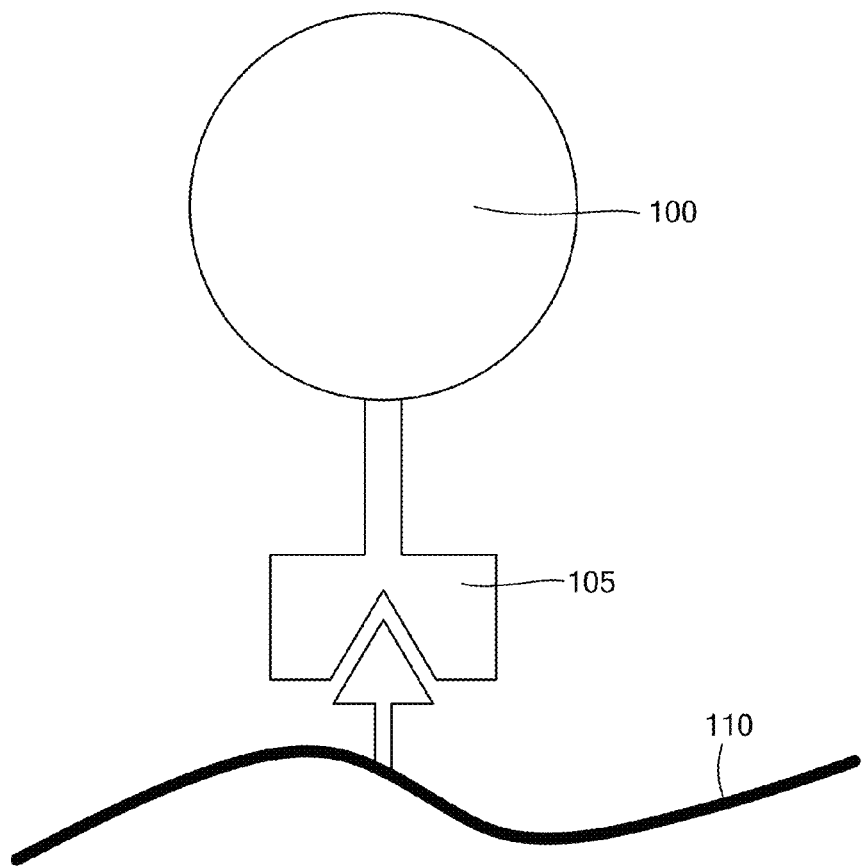
FIG. 1 is a schematic depiction of the linking of a scattering probe to a specific molecular analyte, as employed in accordance with various embodiments of the present invention.

Rather than using time as the extra dimension, as in PALM or STORM, the extra dimension in accordance with the present invention is frequency. In methods of the present invention, scattering probes 100 having distinguishable spectral features are attached to specific molecular analytes 105 by means of selective linkers 110, as shown in FIG. 1. The location of all the scattering probes is then determined by fitting the distinct spectral responses contemporaneously.

By means of spectrally distinguishable nanoprobes, the precision of mapping seen in PALM/STORM may be advantageously achieved with fast measurements and high throughput. By working in the spectral domain rather than the time domain to obtain measurements of individual probe signals, the limitations now seemingly inherent in super-resolved PALM/STORM imaging are addressed. Rather than employing long-time-integrated fluorescence, as in PALM/STORM, the field coherently scattered from nanoprobes of spectrally distinguishable optical response is employed, thereby allowing data to be collected over short integration times.

The signal associated with each individual nanoprobe may be obtained by projection of the total signal onto the spectral response of each probe at each pixel in the raw data. The location of each of the probes can be determined by finding the centroid of the projected signal, in a manner analogous to that performed in PALM/STORM with signals separated in time. Since the measurement is not limited by the need to excite probes at low light levels, SNR can be increased by simply increasing the power of the illuminating light. Instead of SNR, stability, or available time, the only physical limiting factor to the spatial resolution in methods in accordance with the present invention is the physical size of the scattering probes, which limits the packing density.

Spectral diversity in coherent scattering among distinct probes may be engineered by a number of means, all of which are within the scope of the present invention as claimed. For instance, plasmon resonances can be tuned by controlling the gold-silver ratio in alloy spherical nanoparticles, as shown by Link, et al., *Alloy Formation of Gold and Silver Nanoparticles and the Dependence of the Plasmon Absorption on Their*

*Composition, J. Phys. Chem. B*, 103, 3529-33 (1999), which is incorporated herein by reference.

Alternatively, resonances may be tuned by nanoscale structuring of the probe, as described in the following references, all incorporated herein by reference:

Guillon et al., *Coherent Acoustic Vibration of Metal Nanoshells*, Nano Lett., 7, pp. 138-42 (2007);

Kodali et al., *Optimized nanospherical layered alternating metal-dielectric probes for optical sensing*, PNAS, 107, pp. 13620-25 (2010);

Pilo-Pais et al., *Connecting the nano dots: programmable nano fabrication of fused metal shapes on DNA templates*, Nano Lett., 11, pp. 3489-92 (2011); and Chen et al., *Silica-coated Gold Nanorods as Photoacoustic Signal Nano-amplifiers*, Nano Lett., 11, pp. 348-54, (2011).

The signal from individual nanoprobes may be isolated in the spectral domain, as now demonstrated, even when several probes are located in a single focal volume. A generic far-field imaging system in accordance with an embodiment of the present invention, and designated generally by numeral 200, is now described with reference to FIG. 2 in which a collection of nanoprobes 100 have been embedded in a sample 205 and are illuminated by an illuminating electromagnetic wave comprised of broadband radiation 210. The field is coherently scattered and focused, by optic 212, onto a detector 214 in detector plane 216 in the far-zone of the sample. The power spectral density of the field is measured on the detector plane as a function of the position r and wavenumber k. FIGS. 4A-4E depict resulting total intensity and the spectrally-resolved signals. Classical optical theory is used to describe the focusing of light by the optical system, and the interaction between focused light and the spherical nanoprobes with known radius and optical properties. Scalar fields are described here, but the analysis is readily generalized to vector fields within the scope of the present invention as claimed.

The optical properties of each sphere are encoded in the complex refractive index n(k), where the imaginary part determines the absorption properties of the material. The incident field is taken to consist of a superposition of plane waves $e^{ik_i \cdot r}$ integrated over all directions $k_i$ that lie within the solid angle of the focusing optics i.e., Debye focusing, which is implemented, in simulation, using a MonteCarlo approach. More explicitly, $U_{inc}(r,k) = \int d\Omega e^{ik(\hat{\Omega}) \cdot r} = \Omega/N \sum_{i=1}^{N} e^{ik_i \cdot r}$, where $\Omega$ is the solid angle of the focusing optics and N is the number of MonteCarlo samples. For each plane wave, the usual partial wave expansion is made, $e^{ik_i \cdot r} = \sum_{l=0} (2l+1) i^l j_l(kr) P_l[\cos(\hat{k}_i \cdot \hat{r}]$, where $\hat{k}_i$ and $\hat{r}$ are unit vectors in the direction of $k_i$ and r respectively, $j_l$ is the spherical Bessel function of the first kind and $P_l$ is the Legendre polynomial of order l.

For P scatterers in the focal region, the total field is the sum of incident and scattered fields, $U(r) = U_{inc}(r) + \sum_{j=1}^{P} U_j(r)$, where $U_j$ is the scattered field produced by the jth scatterer. For a sphere located at $r_j$, in the plane z=0, the field in the far zone is given by $U_j(r,k) \approx \Omega/N \sum_{i=1}^{N} \sum_{l=0}^{\infty} e^{ik_i \cdot r_j} B_l h_l^{(1)}(kr) P_l[\cos(\hat{k}_i \cdot \hat{r})]$, where $h_l^{(1)}$ is the spherical Hankel function of order l. $B_l$ is determined by enforcing the appropriate boundary conditions, $$B_l = (2l+1) i^l \frac{n j_l(ka) j_l'(kna) - j_l(kna) j_l'(ka)}{h_l'^{(1)}(ka) j_l(kna) - n h_l^{(1)}(ka) j_l'(kna)},$$

where the prime indicates differentiation with respect to the argument in parentheses. It is assumed that there is no interaction between different spheres.

Figure 2:
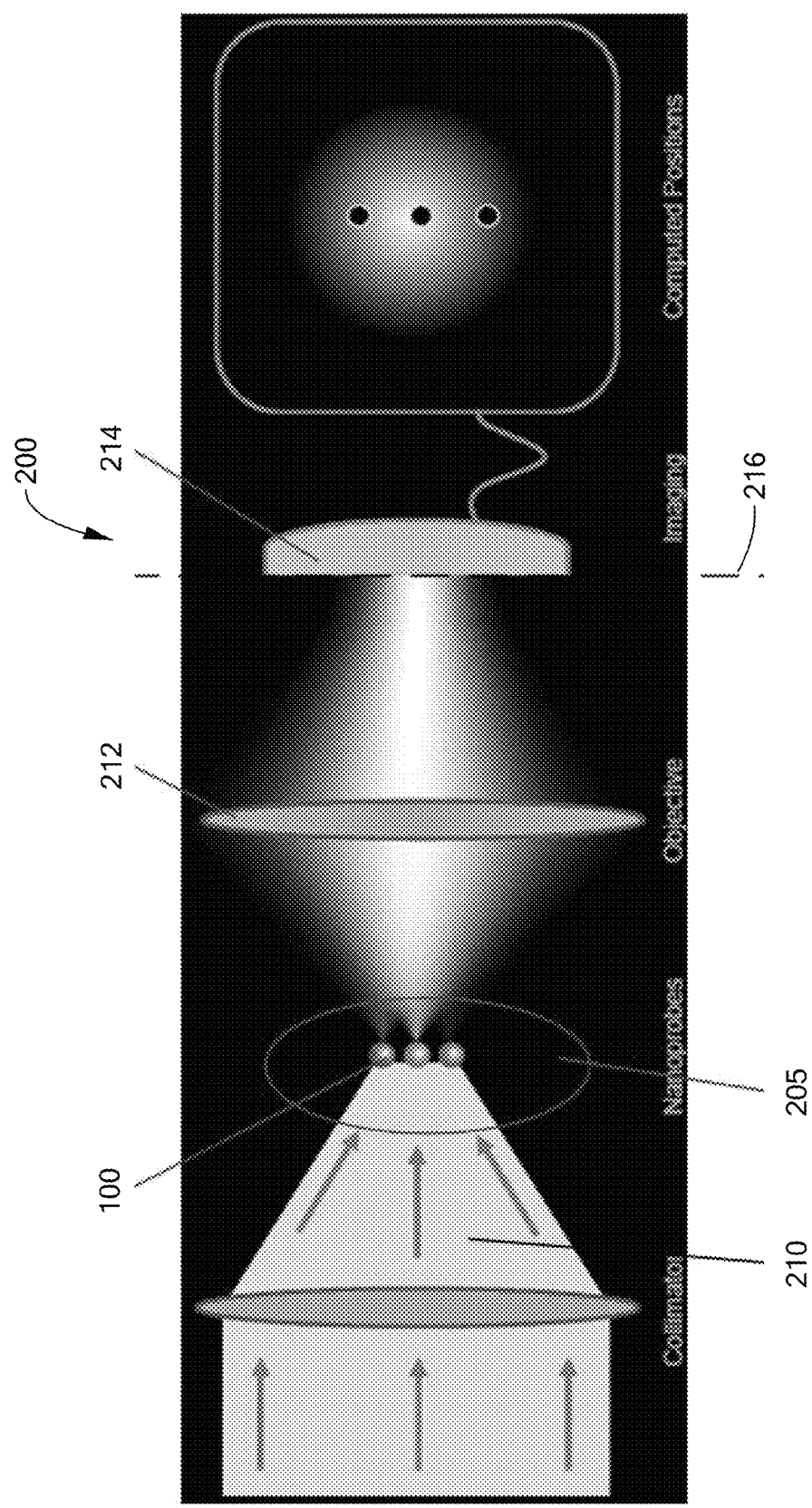
FIG. 2 is a schematic depiction of an imaging system in accordance with embodiments of the present invention, in which the positions of a collection of nanoprobes are retrieved using the described method.

The scattered field is collected and imaged to detector plane 216 as shown in FIG. 2. The focused field is a band-pass limited version of the field at the plane of the sample consistent with the numerical aperture (NA) of the imaging system, here taken to be NA=0.8. The recorded absorbance is given by $$A(r,k) = -\log_{10}\left[\frac{I_S(r,k)}{I_0(r,k)}\right],$$

where $I_0(r, k)$ is the power spectral density of a background measurement with no sample present, and the measurement taken with the sample is denoted by $I_S(r, k)$.

Figure 3:
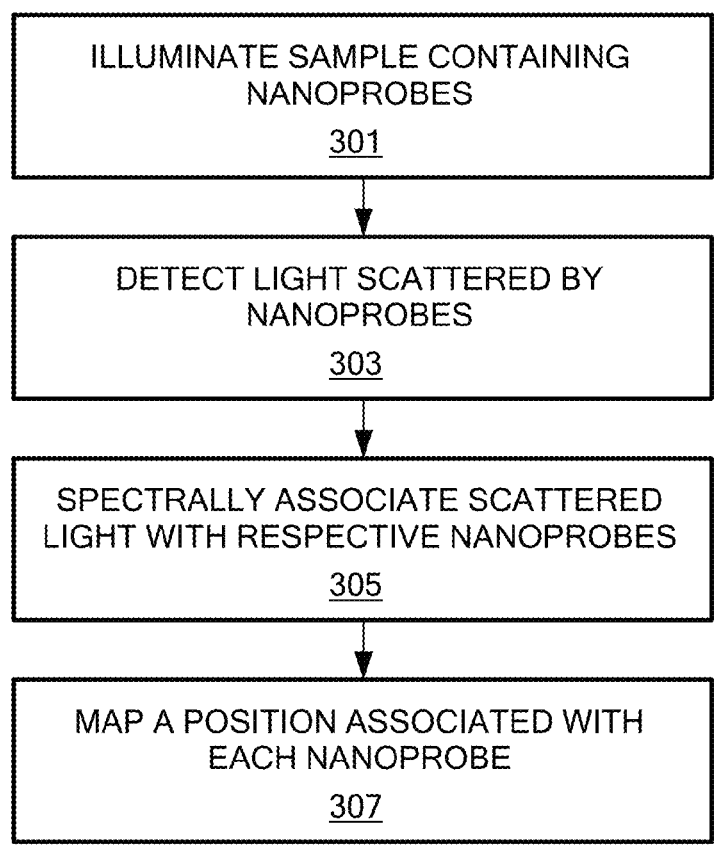
FIG. 3 is a flow chart of a method for mapping positions of nanoprobes using the system of FIG. 2 in accordance with an embodiment of the present invention.

Steps in accordance with methods of the present invention are depicted in FIG. 3. Sample 205 containing nanoprobes 100 (shown in FIG. 2) is illuminated 301 by a broadband source, chosen as appropriate for a particular application. Thus, the broadband source may be a flash lamp, for example. Light scattered by the nanoprobes is collected, focused and detected 303 at detector 214. Detection occurs over the course of a time interval governed by detector response or by integrating electronics, the time interval constituting a "single measurement." The scattered light is spectrally associated 305 with respective nanoprobes and a position associated with each nanoprobe is mapped 307, in two or in three dimensions, using mapping techniques known in the art.

Figure 4E:
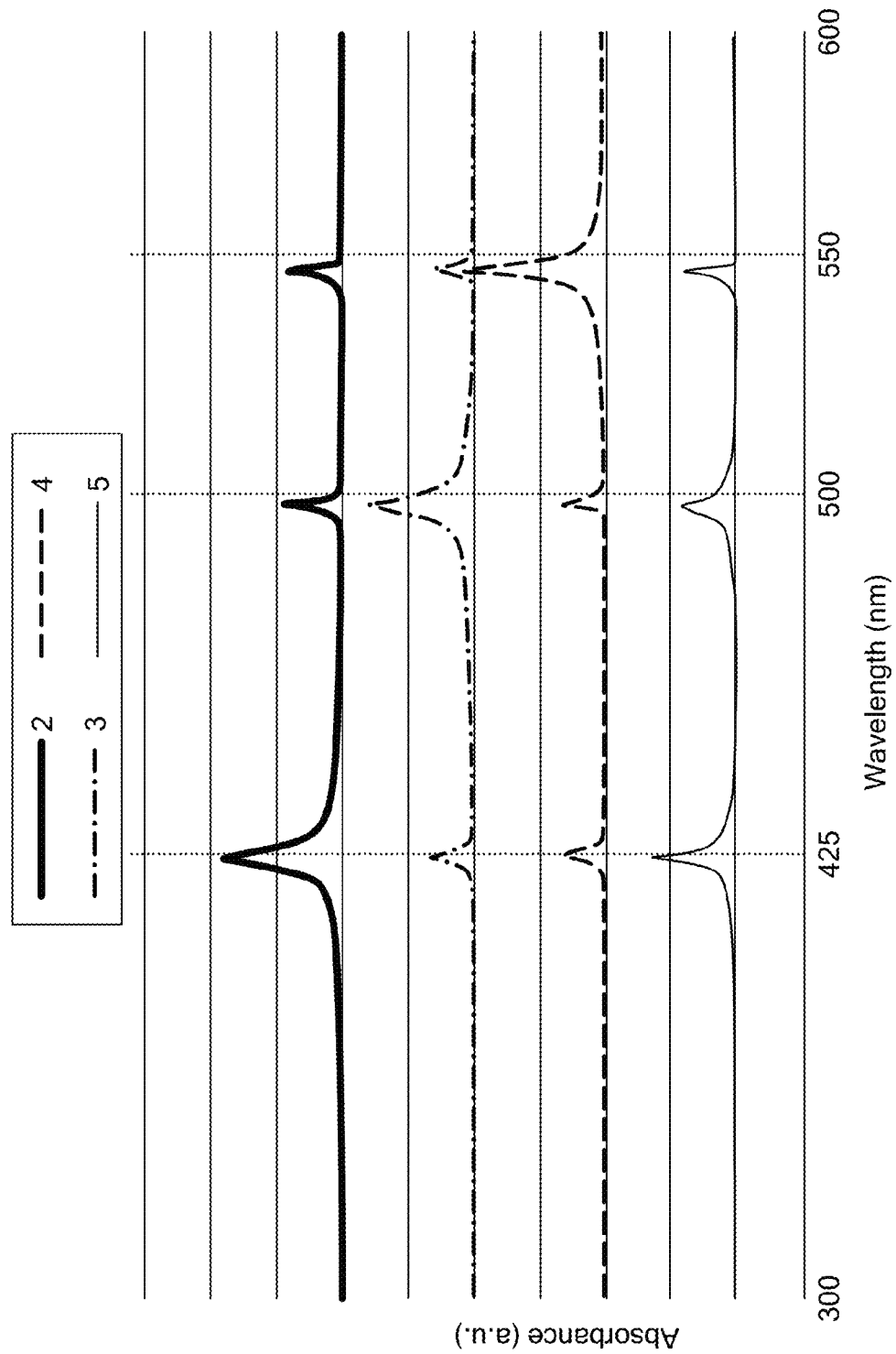

FIGS. 4A-4E show use of the forward model described above to predict the absorbance image arising due to four nanoprobes. The spheres have a radius of 50 nm. Each sphere is taken to have a constant index of refraction n=1.48 plus a single strong absorption peak at λ=425 nm, 500 nm and 550 nm with two nanoprobes at 500 nm and one at each of the other two frequencies. The nanoprobes are arranged so that there is a cluster of three spheres with nearest neighbors separated by 150 nm and a sphere separated from this cluster by 450 nm. FIG. 4A shows the total intensity recorded at the detector plane. The field of view is 2 μm×2 μm. Only two resolvable objects appear in FIG. 4A: a first feature 401 corresponding to nanoprobe 1, while nanoprobes 2, 3 and 4 having merged into a single second feature 402. The application of spectroscopic imaging for super-resolution is demonstrated in FIGS. 4B-4D. The signal from the two identical nanoprobes dominates the total measurement at λ=425 nm (shown in FIG. 4B), but has little effect on the images at λ=500 nm (shown in FIG. 4C) and 550 nm (FIG. 4D) where the signal from the other two spheres is apparent. Thus, using spectrally distinct nanoprobes, the signal from each probe may be isolated even when the probe spacing is smaller than the resolution of the system. This allows mapping of the position of the center of each probe, as is performed in PALM/STORM, for example, with a precision much smaller than the diffraction limited resolution of the imaging system.

A number of considerations arise in identifying the signal from individual probes in coherent scattering which are not issues in fluorescence. The structure and spectral responses of optical scattering nanoprobes are coupled and the recorded spectra are different from the bulk material spectra. Reducing the size of the nanoprobes reduces the frequency of the Mie oscillations, effectively minimizing the intermingling of material properties and the structure. Furthermore, we envision the use of nanoprobes whose spectral responses are perhaps overlapping but distinguishable by projecting the entire spectrum onto a set of appropriate basis functions. Since the contribution of each nanoprobe to the measured image depends in a nonseparable manner on both frequency and position, the position of the nanoprobe and its signal must, in general, be estimated simultaneously. This may be accomplished by a number of iterative methods. For instance, starting with an initial guess of position, the forward model above may be used to predict the recorded fields and the $l^2$ norm of the difference of the measured signal and the predicted one may be minimized with respect to the variation in the nanoprobe position.

Any coherent scattering process may be employed, within the scope of the present invention, whether elastic or inelastic. Thus, Raman scattering, or any higher-order process may be employed. Interferometric detection may also be employed, within the scope of the present invention, using a reference beam derived from the illumination source.

As is evident from the description above, the signal at a nanoprobe resonant frequency is dominated by that nanoprobe. In the event that each nanoprobe is associated with an isolated peak in the spectrum (as above), the identification of a single nanoprobe signal is simplified. This comes at the price of neglecting any data available at other frequencies, but it eliminates the need for an iterative process. Subsequently, the location of the corresponding nanoprobe may be determined, as is done in PALM/STORM, by finding the center of the intensity pattern at that frequency as shown below.

Figures 5A, 5B:
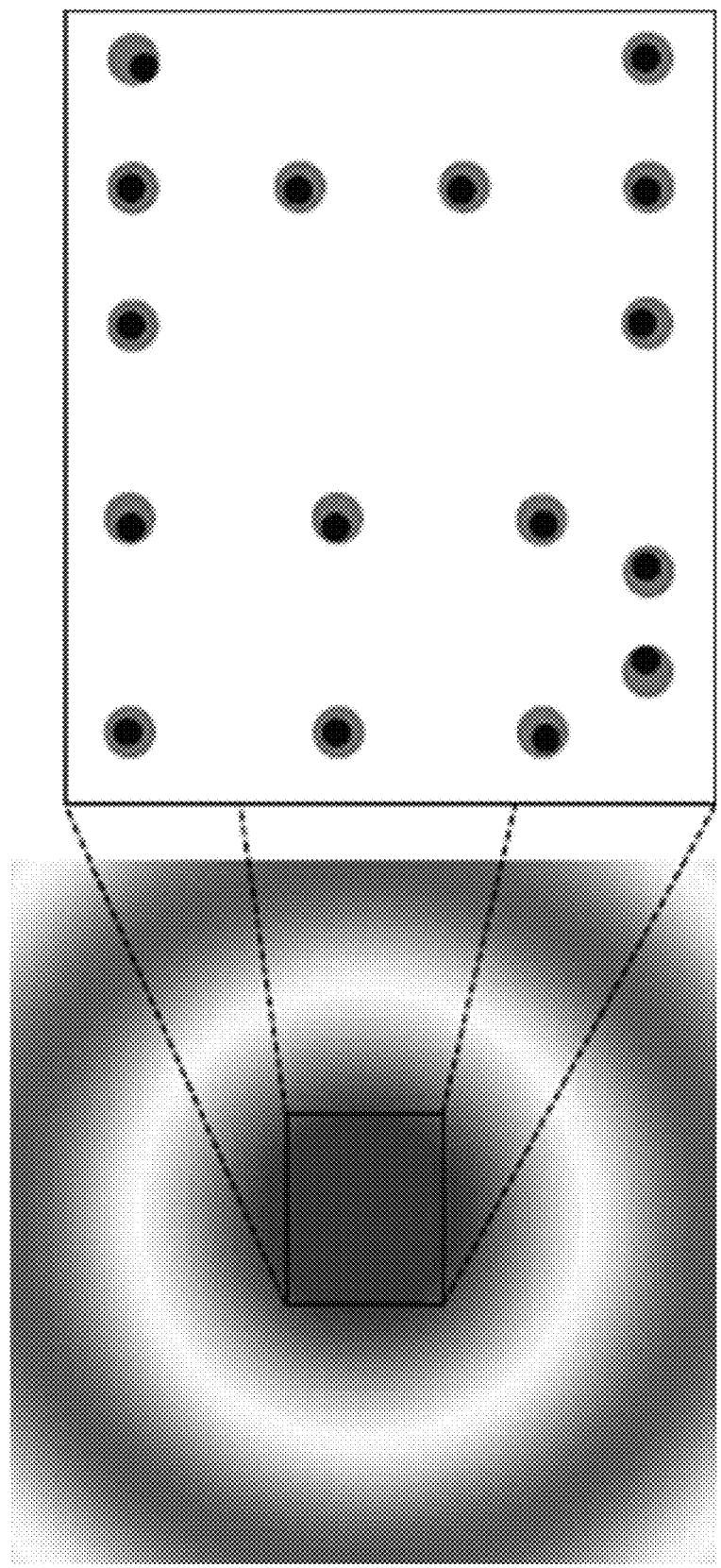
FIGS. 5A-5B are absorbance images of 16 spheres with a radius of 10 nm, with a total field of view of 1 μm×1 μm.

FIGS. 5A-5B demonstrate a simulation of super-resolved mapping in coherent scattering from nanoprobes. The absorbance image of 16 spheres with a radius of 10 nm each, all with distinct, nonoverlapping spectral responses, and all placed within the diffraction-limited focal spot, is shown. The absorption peaks are arranged between wavelengths of 410 nm and 570 nm, separated by 11 nm intervals. This is the approximate range and spectral resolution achievable by varying the gold-silver ratio in alloy spherical nanoparticles, as discussed in Link (1999). The imaging system has a numerical aperture of 0.8. The nanoprobes are all unresolvable as may be seen from the image which appears as a single diffraction-limited spot in FIG. 5A. The signal from each nanoprobe is identified at its resonant frequency, as in FIGS. 4A-4E. The position was estimated by finding the centroid of each signal by Gaussian fitting and mapped in FIG. 5B. The resultant image matches the original distribution and forms the letters "UI". The simulation was performed with a realistic SNR of 10, demonstrating the feasibility of the method.

The present invention may be embodied in any number of instrument modalities. In alternative embodiments, the disclosed methods for super-resolved mapping of nanoprobes may be implemented as a computer program product for use with a computer system. Such implementations may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product). These and other variations and modifications are within the scope of the present invention as defined in any appended claims.

We claim:

1. A method for simultaneously mapping positions of a plurality of spectrally distinguishable nanoprobes with resolution greater than diffraction-limited resolution, the method comprising:
   a. illuminating the plurality of nanoprobes with an illuminating electromagnetic wave;
   b. detecting light scattered by the plurality of nanoprobes;
   c. spectrally associating coherently scattered light with respective nanoprobes; and
   d. mapping, based on a single measurement and coherence of the coherently scattered light, a position associated with each nanoprobe.

2. The method of claim 1, wherein the spectrally distinguishable nanoprobes are linked to at least one specified analyte.

3. The method of claim 1, wherein the spectrally distinguishable nanoprobes are microspheres.

4. The method of claim 1, wherein spectrally associating includes projection of the total signal onto a spectral response of each nanoprobe at each of a plurality of pixels.

5. The method of claim 1, wherein mapping a position includes mapping a position in three dimensions.

6. The method of claim 1, wherein spectrally associating coherently scattered light with respective nanoprobes includes spectrally associating inelastically scattered light.

7. A computer program product for use on a computer system for mapping positions of a plurality of nanoprobes embedded within a sample, the computer program product comprising a computer usable medium having computer-readable non-transitory program code thereon, the computer-readable nontransitory program code including:
   a. program code for spectrally associating coherently scattered light with respective nanoprobes; and
   b. mapping, based on a single measurement and coherence of the coherently scattered light, a position associated with each nanoprobe.

8. The computer program product of claim 7, wherein spectrally associating includes projection of the total signal onto a spectral response of each nanoprobe at each of a plurality of pixels.

9. The computer program product of claim 7, wherein mapping a position includes mapping a position in three dimensions.

* * * * *

UNITED STATES PATENT AND TRADEMARK OFFICE
CERTIFICATE OF CORRECTION

PATENT NO.        : 8,599,388 B1  
APPLICATION NO.   : 13/667287  
DATED             : December 3, 2013  
INVENTOR(S)       : Thomas van Dijk et al.

Page 1 of 1

It is certified that error appears in the above-identified patent and that said Letters Patent is hereby corrected as shown below:

On the title page in item 72 Inventors:

Replace "Thpomas van Dijk"
With "Thomas van Dijk"

Signed and Sealed this
Thirteenth Day of May, 2014

Michelle K. Lee
*Deputy Director of the United States Patent and Trademark Office*